United States Patent
Shintou et al.

(10) Patent No.: US 9,934,882 B2
(45) Date of Patent: Apr. 3, 2018

(54) AMINE COMPOUND AND IONIC CONDUCTIVE AGENT, AND ELECTROCONDUCTIVE RESIN COMPOSITION

(71) Applicant: CANON KABUSHIKI KAISHA, Tokyo (JP)

(72) Inventors: Taichi Shintou, Saitama (JP); Kazuhiro Yamauchi, Suntou-gun (JP); Satoru Nishioka, Suntou-gun (JP); Takeshi Miyazaki, Ebina (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 262 days.

(21) Appl. No.: 14/708,515

(22) Filed: May 11, 2015

(65) Prior Publication Data

US 2015/0329474 A1   Nov. 19, 2015

(30) Foreign Application Priority Data

May 15, 2014   (JP) .................................. 2014-101636
Apr. 9, 2015   (JP) .................................. 2015-080042

(51) Int. Cl.

| | |
|---|---|
| *H01B 1/20* | (2006.01) |
| *H01B 1/12* | (2006.01) |
| *C07C 211/13* | (2006.01) |
| *C07C 211/14* | (2006.01) |
| *C07C 211/18* | (2006.01) |
| *C07C 211/63* | (2006.01) |
| *C07C 311/09* | (2006.01) |
| *C07C 311/10* | (2006.01) |
| *C07C 311/48* | (2006.01) |
| *C07D 285/15* | (2006.01) |
| *C07D 233/61* | (2006.01) |
| *C07D 295/13* | (2006.01) |
| *C07D 213/18* | (2006.01) |
| *C08G 18/64* | (2006.01) |
| *C08G 18/32* | (2006.01) |
| *C08G 18/40* | (2006.01) |
| *C08G 18/48* | (2006.01) |

(52) U.S. Cl.
CPC .............. *H01B 1/20* (2013.01); *C07C 211/13* (2013.01); *C07C 211/14* (2013.01); *C07C 211/18* (2013.01); *C07C 211/63* (2013.01); *C07C 311/09* (2013.01); *C07C 311/10* (2013.01); *C07C 311/48* (2013.01); *C07D 213/18* (2013.01); *C07D 233/61* (2013.01); *C07D 285/15* (2013.01); *C07D 295/13* (2013.01); *C08G 18/3268* (2013.01); *C08G 18/4081* (2013.01); *C08G 18/48* (2013.01); *C08G 18/6423* (2013.01); *H01B 1/122* (2013.01); *H01B 1/125* (2013.01)

(58) Field of Classification Search
CPC .......... H01B 1/12; H01B 1/121; H01B 1/122; H01B 1/124; H01B 1/125; H01B 1/20; C07D 207/06; C07D 233/61; C07D 285/15; C07D 295/13; C07C 211/13; C07C 211/14; C07C 211/18; C07C 211/36; C07C 211/62; C07C 211/63; C07C 311/00; C07C 311/09; C07C 311/10; C07C 311/31; C07C 311/32; C07C 311/48
See application file for complete search history.

(56) References Cited

U.S. PATENT DOCUMENTS

| | | | | |
|---|---|---|---|---|
| 3,968,315 | A * | 7/1976 | Hochreuter | C09K 3/16 427/394 |
| 4,362,886 | A * | 12/1982 | Ford | C07D 295/13 544/359 |
| 6,992,045 | B2 | 1/2006 | Xu et al. | |
| 7,208,605 | B2 | 4/2007 | Davis, Jr. | |
| 7,608,142 | B2 * | 10/2009 | Thorstensson | C07C 211/14 106/277 |

(Continued)

FOREIGN PATENT DOCUMENTS

| | | |
|---|---|---|
| JP | 2006-500418 A | 1/2006 |
| JP | 2006-040659 A | 2/2006 |

(Continued)

OTHER PUBLICATIONS

U.S. Appl. No. 14/701,837, filed May 1, 2015, Shintou et al.

(Continued)

*Primary Examiner* — Harold Pyon
*Assistant Examiner* — Matthew R Diaz
(74) *Attorney, Agent, or Firm* — Fitzpatrick, Cella, Harper & Scinto (57) ABSTRACT

An amine compound and an ionic conductive agent excellent in electroconductivity are provided. By using the amine compound, an electroconductive resin composition suppressed in bleeding and excellent in electroconductivity is provided. The amine compound and the ionic conductive agent have a structure represented by the following general formula (1).

General Formula (1)

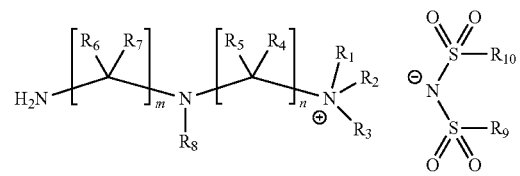

7 Claims, 1 Drawing Sheet

(56) References Cited

U.S. PATENT DOCUMENTS

| | | |
|---|---|---|
| 7,744,838 B2 | 6/2010 | Davis, Jr. |
| 8,053,589 B1 | 11/2011 | McArdle et al. |
| 8,227,641 B2 * | 7/2012 | Rampf ............... C07C 209/48 564/491 |
| 8,628,854 B2 | 1/2014 | Yamauchi et al. |
| 8,674,135 B2 | 3/2014 | Davis, Jr. |
| 8,771,818 B2 | 7/2014 | Nishioka et al. |
| 8,852,743 B2 | 10/2014 | Kikuchi et al. |
| 2006/0128996 A1 | 6/2006 | Vaultier et al. |
| 2007/0185330 A1 | 8/2007 | Walker |
| 2008/0221361 A1 | 9/2008 | Walker |
| 2009/0045373 A1 | 2/2009 | Hammami et al. |
| 2009/0326228 A1 | 12/2009 | Vaultier et al. |
| 2010/0152465 A1 | 6/2010 | Davis, Jr. |
| 2010/0158818 A1 * | 6/2010 | Jain .................. A61K 31/14 424/45 |
| 2011/0045359 A1 * | 2/2011 | Schmidt ............ C07C 211/63 429/338 |
| 2012/0052572 A1 * | 3/2012 | Whitney ............. C12Q 1/6806 435/372 |
| 2012/0308882 A1 * | 12/2012 | Ito ..................... C07D 207/06 429/200 |
| 2013/0156992 A1 | 6/2013 | Okumura et al. |
| 2013/0281276 A1 | 10/2013 | Watanabe et al. |
| 2013/0323155 A1 | 12/2013 | Tsubokura et al. |
| 2015/0332803 A1 | 11/2015 | Shintou et al. |

FOREIGN PATENT DOCUMENTS

| | | |
|---|---|---|
| JP | 2006-206517 A1 | 8/2006 |
| JP | 2009-144051 A | 7/2009 |
| WO | 03/086605 A2 | 10/2003 |
| WO | 2013/094163 A1 | 6/2013 |
| WO | 2013/099146 A1 | 7/2013 |
| WO | 2013/099188 A1 | 7/2013 |
| WO | 2013/099207 A1 | 7/2013 |

OTHER PUBLICATIONS

Office Action in German Patent Application No. 10 2015 107 514.8 (dated Jul. 13, 2016).

M. Niyaz Khan et al., "Kinetic Evidence for the Occurrence of a Stepwise Mechanism in Hydrazinolysis of Phthalimide," 60 J. Org. Chem. 4536-4541 (1995).

* cited by examiner

AMINE COMPOUND AND IONIC CONDUCTIVE AGENT, AND ELECTROCONDUCTIVE RESIN COMPOSITION

BACKGROUND OF THE INVENTION

Field of the Invention

The present invention relates to an amine compound and an ionic conductive agent, and an electroconductive resin composition.

Description of the Related Art

In recent years, synthetic resins have been utilized in various fields of liquid crystal displays, precision devices such as optical lenses, automobile parts, base materials for magnetic recording media such as optical discs, protection films for materials for semiconductors, and the like. Synthetic resins, though being lightweight and excellent in toughness as compared with glass products, have problems of being liable to be charged and to cause dusts to easily adhere thereto. In order to solve this, a measure is taken to impart electroconductivity to an electroconductive resin composition, for example, by adding an additive such as an ionic conductive agent to an insulative resin. In this case, since homogeneous dispersion of the additive in the resin is easy, uniform electroconductivity can be imparted to the resin. Such a problem (bleeding) arises, however, that along with the lapse of time, the ionic conductive agent present in the resin migrates to the resin surface, and sometimes generates tackiness on the surface and contaminates contacted materials.

In order to solve these problems, for example, an ionic conductive agent having a terminal hydroxyl group is reported (Japanese Patent Application Laid-Open No. 2009-144051). The Patent Literature is not satisfactory, however, in order to sufficiently solve the problem that the ionic conductive agent present in the resin migrates to the resin surface along with the lapse of time; and the development of an ionic conductive agent good in the reactivity with a resin is further demanded. On the other hand, although ionic conductive agents having an amino group on the terminal are known, the applications are limited to solvents and the purification of synthetic reactions (U.S. Pat. No. 8,053,589, Japanese Patent Application Laid-Open No. 2006-500418 and International Publication No. WO2003/086605).

SUMMARY OF THE INVENTION

One embodiment of the present invention is directed to providing an amine compound and an ionic conductive agent excellent in electroconductivity. Another embodiment of the present invention is directed to providing an electroconductive resin composition suppressed in bleeding and excellent in electroconductivity by using the amine compound.

According to one aspect of the present invention, there is provided an amine compound having a structure represented by the following general formula (1).

General Formula (1)

In the general formula (1), $R_1$ to $R_3$ each independently denote a substituted or unsubstituted alkyl group having 1 or more and 20 or less carbon atoms, or a group of atoms necessary for forming a ring structure together with one nitrogen atom by bonding of any two selected from $R_1$ to $R_3$;

$R_4$ to $R_7$ each independently denote a hydrogen atom, or a substituted or unsubstituted alkyl group having 1 or more and 20 or less carbon atoms;

$R_8$ denotes a hydrogen atom, a substituted or unsubstituted alkyl group having 1 or more and 20 or less carbon atoms, or a substituted or unsubstituted aminoalkyl group having 1 or more and 20 or less carbon atoms; and $R_9$ and $R_{10}$ each independently denote a fluorine atom, or a perfluoroalkyl group having 1 or more and 8 or less carbon atoms, or a group of atoms necessary for forming a ring structure containing a fluorine atom(s) together with two sulfur atoms and one nitrogen atom by mutually bonding of $R_9$ and $R_{10}$.

n and m each independently denote an integer of 1 to 20.

According to another aspect of the present invention, there is provided an ionic conductive agent and an electroconductive resin composition containing the above amine compound.

According to further aspect of the present invention, there is provided an electroconductive resin composition comprising a crosslinked product of the above amine compound and a polyisocyanate compound.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

As a result of studies, the present inventors have found that an amine compound having a structure represented by the following general formula (1) is excellent in electroconductivity. It also has been found that the amine compound makes an ionic conductive agent, and this finding has led to the present invention. It has further been found that an electroconductive resin composition obtained by crosslinking the amine compound and a resin, since the amine compound is immobilized to the resin, is suppressed in bleeding and excellent in electroconductivity, and this finding has led to the present invention.

General Formula (1)

In the general formula (1), $R_1$ to $R_3$ each independently denote a substituted or unsubstituted alkyl group having 1 or more and 20 or less carbon atoms, or a group of atoms necessary for forming a ring structure together with one nitrogen atom by bonding of any two selected from $R_1$ to $R_3$;

$R_4$ to $R_7$ each independently denote a hydrogen atom, or a substituted or unsubstituted alkyl group having 1 or more and 20 or less carbon atoms;

$R_8$ denotes a hydrogen atom, a substituted or unsubstituted alkyl group having 1 or more and 20 or less carbon atoms, or a substituted or unsubstituted aminoalkyl group having 1 or more and 20 or less carbon atoms; and $R_9$ and $R_{10}$ each independently denote a fluorine atom, or a perfluoroalkyl group having 1 or more and 8 or less carbon atoms, or a group of atoms necessary for forming a ring structure containing a fluorine atom(s) together with two sulfur atoms and one nitrogen atom by mutual bonding of $R_9$ and $R_{10}$.

n and m each independently denote an integer of 1 to 20.

First, amine compounds represented by the general formula (1) will be described.

In the general formula (1), the alkyl groups in $R_1$ to $R_3$ are not especially limited, but examples thereof include saturated or unsaturated, linear, branched or cyclic, primary to tertiary alkyl groups having 1 to 20 carbon atoms such as a methyl group, an ethyl group, a n-propyl group, an isopropyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl group, 2-ethylhexyl group and a cyclohexenylethyl group. The cases of alkyl groups having 1 or more and 4 or less carbon atoms, such as a methyl group, an ethyl group, a n-propyl group, an isopropyl group and a n-butyl group, are especially preferable, and the case of a methyl group is especially preferable because of being excellent in electroconductivity.

In the general formula (1), the ring formed together with one nitrogen atom by bonding of any two selected from $R_1$ to $R_3$ is not especially limited, but includes a pyrrolidine ring, a pyridine ring, an indazoline ring, a 1,4-diazabicyclo [2.2.2]octane ring and a piperidine ring.

In the general formula (1), the alkyl groups in $R_4$ to $R_7$ are not especially limited, but examples thereof include saturated or unsaturated, linear, branched or cyclic, primary to tertiary alkyl groups having 1 to 20 carbon atoms such as a methyl group, an ethyl group, a n-propyl group, an isopropyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group and a cyclohexenylethyl group.

$R_4$ to $R_8$ are preferably a hydrogen atom because this case is excellent in electroconductivity.

In the general formula (1), the alkyl group in $R_8$ is not especially limited, but examples thereof include saturated or unsaturated, linear, branched or cyclic, primary to tertiary alkyl groups having 1 to 20 carbon atoms such as a methyl group, an ethyl group, a n-propyl group, an isopropyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, a 2-ethylhexyl group and a cyclohexenylethyl group.

In the general formula (1), the aminoalkyl group in $R_8$ is not especially limited, but examples thereof include an aminoethyl group, an aminobutyl group, an aminooctyl group, an aminododecyl group and an aminononadecyl group.

In the general formula (1), the aminoalkyl group in $R_8$ is especially preferably the same as the other terminal amino group as shown in the following general formula (2), because this case is excellent in electroconductivity.

General Formula (2)

In the general formula (1), the perfluoroalkyl groups in $R_9$ and $R_{10}$ are not especially limited, but examples thereof include a trifluoromethyl group, a perfluoroethyl group, a perfluoropropyl group, a perfluorobutyl group and a perfluorooctyl group. The perfluoroalkyl group is especially preferably a trifluoromethyl group or a perfluoroethyl group, because this case is excellent in electroconductivity.

In the general formula (1), the ring containing a fluorine atom(s) formed together with two sulfur atoms and one nitrogen atom by mutual bonding of $R_9$ and $R_{10}$ is not especially limited, but includes the following structure.

The amine compound having a structure represented by the general formula (1) can be synthesized by reference to a well-known method of combining Journal of Organic Chemistry, 1995, 60, 4536-4541 (Gabriel reaction), synthesis of a halogenated quaternary ammonium salt by a nucleophilic reaction of a tertiary amine to an alkyl halide, anion exchange reaction between a halogenated quaternary ammonium salt and an alkaline metal salt of a fluorine-based anionic compound, and the like.

One mode of a method for producing an amine compound having a structure represented by the above general formula (1) will be shown below, but the production method is not limited thereto.

Here, $R_1$ to $R_{10}$ and n and m of each compound in the above reaction formulae and the compound having a structure represented by the general formula (1) are the same as described before. M denotes an alkaline metal such as Li, K and Na.

That is, the amine compound represented by the general formula (1) can be obtained through (1) an amination step, (2) a halogen substitution step, (3) a quaternary salt-making step, (4) a deprotection step (Gabriel reaction step), and (5) a salt exchange step (anion exchange step).

<About (1) an Amination Step>
First, an amination step of obtaining a tertiary amine intermediate (1) will be described.

The amination step is a step of reacting an aminoalcohol with a halogen compound to thereby obtain a tertiary amine intermediate (1).

The amination step may be carried out as a solventless reaction, but can be carried out in the presence of a solvent. The solvent is not especially limited as long as not participating in the reaction, and examples thereof include acetonitrile, heptane, toluene and N,N-dimethylformamide (hereinafter, abbreviated to DMF). Also two or more solvents may be mixed and used, and the mixing ratio in the mixing usage can be determined arbitrarily. DMF is especially preferable.

The amount of the above solvent to be used is, with respect to an aminoalcohol, preferably in the range of 0.1 to 1,000% by mass, and more preferably 1.0 to 150% by mass.

Further in the amination step, in order to quickly proceed the reaction, a base can be used. The base usable is not especially limited as long as not participating in the reaction, but examples thereof include inorganic bases such as sodium carbonate, sodium hydrogencarbonate, barium carbonate, calcium carbonate and potassium carbonate. The amount of the base to be used is, with respect to an aminoalcohol, preferably in the range of 0.01 to 100% by mass, more preferably 0.1 to 20% by mass, and still more preferably 0.5 to 5% by mass. A desired tertiary amine intermediate (1) can be obtained by carrying out purification such as recrystallization or silica gel chromatography after the termination of the reaction.

The reaction temperature in the amination step is preferably in the range of −20° C. to 250° C., and more preferably 0° C. to 150° C. The reaction is completed usually within 48 hours.

<About (2) a Halogen Substitution Step>
Then, a halogen substitution step of obtaining a halide intermediate (1) will be described.

The halogen substitution step is a step of subjecting a halogen atom to a nucleophilic substitution reaction with a hydroxyl group of the tertiary amine intermediate (1) to thereby obtain a halide intermediate (1).

A halogenating agent capable of being used in the halogen substitution step is not especially limited, but examples thereof include thionyl chloride, sulfuryl chloride, phosphorus tribromide, p-toluenesulfonic acid chloride, methanesulfonic acid chloride and carbon tetrabromide. In order to raise the reactivity in the next step, phosphorus tribromide, carbon tetrabromide or the like can be used.

The halogen substitution step may be carried out as a solventless reaction, but can be carried out in the presence of a solvent. The solvent is not especially limited as long as not participating in the reaction, and for example, a halogen-based solvent such as dichloromethane, dichloroethane or chloroform can be used.

The reaction temperature in the halogen substitution step is preferably in the range of −20° C. to 250° C., and more preferably 0° C. to 150° C. The reaction is completed usually within 24 hours.

A desired halide intermediate (1) can be obtained by carrying out purification such as recrystallization or silica gel chromatography after the termination of the reaction.

<About (3) a Quaternary Salt-Making Step>

Then, a quaternary salt-making step of obtaining a quaternary salt intermediate (1) will be described.

The quaternary salt-making step is a step of reacting an alkyl halide with a tertiary amine to thereby obtain a quaternary salt.

The quaternary salt-making step may be carried out as a solventless reaction, but can be carried out in the presence of a solvent. The solvent is not especially limited as long as not participating in the reaction, and examples thereof include acetonitrile, heptane, toluene and DMF. Also two or more solvents may be mixed and used, and the mixing ratio in the mixing usage can be determined arbitrarily. Acetonitrile is especially preferable.

The tertiary amine capable of being used in the quaternary salt-making step is not especially limited, but examples thereof suitably include tertiary amines (1) to (11) shown below.

(1)

tertiary amine

(2)

tertiary amine

(3)

tertiary amine (4)

tertiary amine

(5)

tertiary amine

(6)

tertiary amine

(7)

tertiary amine

(8)

tertiary amine

(9)

tertiary amine (10)

tertiary amine (11)

tertiary amine

Tertiary amines (1), (2), (7) and (10) are especially preferable because they are excellent in electroconductivity.

The reaction temperature in the quaternary salt-making step is preferably in the range of −20° C. to 250° C., and more preferably 0° C. to 150° C. The reaction is completed usually within 48 hours. In the case where the boiling point of the tertiary amine is low, the reaction is carried out using a pressure-resistant closed vessel.

A desired quaternary salt intermediate (1) can be obtained by carrying out purification such as recrystallization or silica gel chromatography after the termination of the reaction.

<About (4) a Deprotection Step (Gabriel Reaction Step)>

Then, a Gabriel reaction step of obtaining a tertiary amine intermediate (2) will be described.

The Gabriel reaction step is a step of reacting the quaternary salt with hydrazine monohydrate to thereby obtain a tertiary amine intermediate (2).

The Gabriel reaction step may be carried out as a solventless reaction, but can be carried out in the presence of a solvent. The solvent is not especially limited as long as not participating in the reaction, and examples thereof include methanol, ethanol, propanol, acetonitrile, heptane, toluene and DMF. Also two or more solvents may be mixed and used, and the mixing ratio in the mixing usage can be determined arbitrarily. Methanol, ethanol and propanol are especially preferable.

The reaction temperature in the Gabriel reaction step is preferably in the range of −20° C. to 250° C., and more preferably 0° C. to 150° C. The reaction is completed usually within 48 hours.

A desired tertiary amine intermediate (2) can be obtained by carrying out purification such as recrystallization or silica gel chromatography after the termination of the reaction.

<About (5) a Salt Exchange Step (Anion Exchange Step)>

An anion exchange step of obtaining one form of the general formula (1) will be described. The anion exchange step is a step of subjecting the tertiary amine intermediate (2) to an anion exchange reaction with an alkaline metal salt of a fluorine-based anionic compound to thereby obtain a target substance.

A solvent to be used in the anion exchange step includes polar solvents such as water, alcohols, acetone and acetonitrile, and nonpolar solvents such as hexane and heptane. A solvent to be used can be selected in consideration of properties of an ionic conductive agent to be produced. For example, in the case where the ionic conductive agent to be produced is water-insoluble, the reaction can be carried out using water as a solvent. Further by washing an obtained reaction liquid with water, a by-produced metal halide salt can easily be removed. By contrast, in the case where the ionic conductive agent to be produced is water-soluble, when a solvent in which a by-produced metal halide salt cannot be dissolved is selected and used, the metal halide salt can easily be removed.

The alkaline metal salt of the fluorine-based anionic compound capable of being used in the anion exchange step is not especially limited, but examples thereof suitably include anionic compounds (1) to (8) shown below.

anionic compound (1)

anionic compound (2)

anionic compound (3)

anionic compound (4)

anionic compound (5)

anionic compound (6)

anionic compound (7)

anionic compound (8)

Anionic compounds (1), (2), (3), (5) and (7) are especially preferable because they are easily handled and excellent in electroconductivity.

Further a scavenger of halogen ions can be used. The scavenger of halogen ions is not especially limited, but includes silver nitrate and ion-exchange resins.

A target substance can be obtained by carrying out purification such as silica gel chromatography after the termination of the reaction.

As preferable examples of the amine compounds according to the present invention, compounds (1) to (11) are shown below, but the amine compounds are not limited to the following compounds.

compound (1)

-continued compound (2)

compound (3)

compound (4)

compound (5)

compound (6)

compound (7)

-continued compound (8)

compound (9)

compound (10)

compound (11)

The amine compound according to the present invention can suitably be used as an ionic conductive agent, because the compound has a property of becoming a fused salt composed of a cation and an anion at least in a fixed temperature range of 0° C. to 300° C.

<About an Electroconductive Resin Composition>

The use of the amine compound according to the present invention can provide an electroconductive resin composition suppressed in bleeding and excellent in electroconductivity.

The electroconductive resin composition according to the present invention will be described.

The electroconductive resin composition can be obtained by directly kneading the amine compound according to the present invention and general-purpose resins such as a thermoplastic resin, an ultraviolet curing resin, a rubber and a pressure-sensitive adhesive. The general-purpose resins mentioned here, such as a thermoplastic resin, an ultraviolet curing resin, a rubber and a pressure-sensitive adhesive, may or may not contain a polyisocyanate group(s) (polyisocyanate compound).

The thermoplastic resin to be used is not especially limited, but examples thereof include polyolefin-based resins, polyacryl resins, polystyrene resins, polyester resins, polyurethane resins, polycarbonate resins, polyvinyl chloride resins and epoxy resins.

The ultraviolet curing resin to be used in the present invention is not especially limited, but an example thereof includes diethylene glycol di(meth)acrylate.

The rubber to be used in the present invention is not especially limited, but examples thereof include acryl rubbers, urethane rubbers, styrene-butadiene copolymer rubbers, epichlorohydrin-ethylene oxide copolymer rubbers, epichlorohydrin-ethylene oxide-allyl glycidyl ether copolymer rubbers, acrylonitrile-butadiene rubbers, epichlorohydrin rubbers and silicone rubbers.

The pressure-sensitive adhesive to be used in the present invention is not especially limited, but includes acryl-based pressure-sensitive adhesives, rubber-based pressure-sensitive adhesives and silicone-based pressure-sensitive adhesives.

The urethane resin can be made also by mixing the amine compound and a polyisocyanate group-containing substance (polyisocyanate compound), and allowing the mixture together with a polyol compound to be crosslinked. In the crosslinked urethane resin, the amine compound is crosslinked with the isocyanate group-containing substance and immobilized in the polymer, i.e. a crosslinked product of the amine compound and the polyisocyanate compound. Hence, the bleeding in which an ionic conductive agent present in the resin migrates to the resin surface along with the lapse of time can be suppressed, and an effect of being excellent in the preservation stability can be attained.

The polyisocyanate group-containing substance is not especially limited as long as having two or more isocyanate groups, but examples thereof include 4,4'-diphenylmethane diisocyanate (MDI), isophorone diisocyanate, 4,4'-dicyclohexyl diisocyanate, trimethylhexamethylene diisocyanate, tolylene diisocyanate, carbodiimide-modified diisocyanate, polymethylene phenyl polyisocyanate, orthotolidine diisocyanate, naphthalene diisocyanate, xylene diisocyanate, hexamethylene diisocyanate, praraphenylene diisocyanate, lysine diisocyanate methyl ester and dimethyl diisocyanate. These may be used singly or in combinations of two or more.

The polyol compound to be used in the present invention is not especially limited as long as having two or more hydroxyl groups. Specifically, a polyether polyol, a polyester polyol, a polycarbonate polyol or the like can be used. Especially preferable is a polyether polyol having an alkylene oxide structure. These may be used singly or in combinations of two or more.

The amount of the amine compound to be used in the electroconductive resin composition to be used in the present invention can suitably be varied according to the degree of a target electroconductivity.

The amount of the amine compound to be used is, with respect to 100 parts by mass of general-purpose resins such as a thermoplastic resin, an ultraviolet curing resin, a rubber and a pressure-sensitive adhesive, in the range of 0.001 to 100 parts by mass, preferably 0.01 to 50 parts by mass, and especially preferably 0.1 to 10 parts by mass.

The amount of the amine compound to be used is, with respect to 100 parts by mass of polyisocyanate group-containing general-purpose resins such as a polyisocyanate group-containing thermoplastic resin, ultraviolet curing resin, rubber and pressure-sensitive adhesive, in the range of 0.001 to 100 parts by mass, preferably 0.5 to 20 parts by mass, and especially preferably 0.5 to 5 parts by mass. The case where the amount to be blended is 0.5 parts by mass or larger can easily provide an effect of imparting electroconductivity by addition of an ion conductive agent. The case of being 5 parts by mass or smaller can reduce the change with time in the electric resistance.

In the electroconductive resin composition according to the present invention, blending agents may be added, in ranges of not impairing the advantage of the present invention, to the polyisocyanate group-containing substance. Examples of the blending agents include pigments, dyes, surfactants, plasticizers, ultraviolet absorbents, fillers, softening agents, processing auxiliary agents, tackifiers, tackiness preventing agents, dispersants and foaming agents.

A molded article of a film form, a sheet form, a roll form or the like can be obtained by kneading the electroconductive resin composition according to the present invention.

As described above, the electroconductive resin composition according to the present invention, since the amine compound according to the present invention is configured by being crosslinked, can provide an electroconductive resin composition suppressed in bleeding and excellent in electroconductivity.

EXAMPLES

Hereinafter, the present invention will be described in detail by way of Examples and Comparative Examples, but the present invention is not limited to these Examples. Here, "parts" and "%" in the description are in terms of mass unless otherwise specified. The identification of obtained compounds was carried out using a $^1H$ nuclear magnetic resonance ($^1H$-NMR) spectrometer (ECA-400, manufactured by JEOL Ltd.) and LC/TOF MS (LC/MSD TOF, manufactured by Agilent Technologies, Inc.).

[Production of an Amine Compound Having a Structure Represented by the General Formula (1)]

An amine compound having a structure represented by the general formula (1) according to the present invention can be synthesized by a well-known method.

The amine compound having a structure represented by the general formula (1) according to the present invention was produced by a method described below.

Production Example 1: Production of a Compound (2)

halide intermediate (1)

(3) quaternary salt-making step quaternary salt (1)

(4) Gabriel reaction step tertiary amine intermediate (2)

(5) anion exchange step 39.5 g (213 mmol) of potassium phthalimide was added to a solution of 50 g (152 mmol) of dibromododecane in 380 mL of dimethylformamide (DMF), and the mixture was stirred at room temperature for 3 days. After the termination of the reaction, the resultant was diluted with 2 L of ethyl acetate, washed with 2 L of water, and then washed with 2 L of saturated brine. An organic layer was washed with anhydrous sodium sulfate, thereafter filtered, and dried under reduced pressure. The resultant was purified by silica gel chromatography to thereby obtain 24.1 g (61 mmol) (yield: 40%) of a halogen compound.

2.86 g (34 mmol) of sodium hydrogencarbonate was added to a solution of 3.42 g (17 mmol) of 12-aminododecanol and 14.7 g (37.3 mmol) of the halogen compound obtained in the above in 34 mL of dimethylformamide, and the mixture was stirred at 100° C. for 18 hours. After the termination of the reaction, the resultant was cooled to room temperature, and diluted with 340 mL of water. The resultant was separated with 340 mL of ethyl acetate; thereafter, an organic layer was washed with 180 mL of water. The organic layer was further washed with 180 mL of saturated brine. The organic layer was washed with anhydrous sodium sulfate, thereafter filtered, and dried under reduced pressure. The resultant was purified by silica gel column chromatography to thereby obtain 7.82 g (9.4 mmol) (yield: 56%) of a tertiary amine intermediate (1).

1.57 g (6.0 mmol) of triphenylphosphine and 2.48 g (7.5 mmol) of carbon tetrabromide were added to a solution of 4.14 g (5.0 mmol) of the tertiary amine intermediate (1) in 50 mL of dichloromethane, and the mixture was stirred at room temperature for 3 hours, under a nitrogen atmosphere. After the termination of the reaction, 100 mL of a saturated sodium hydrogencarbonate aqueous solution was added, and the resultant was extracted with 100 mL of dichloromethane, and further twice extracted with 100 mL of dichloromethane. Organic layers were united, dried with anhydrous sodium sulfate, and thereafter filtered; and the solvent was concentrated under reduced pressure. The resultant was purified by silica gel column chromatography to thereby obtain 3.8 g (4.3 mmol) (yield: 85%) of a halide intermediate (1).

4 mL of a 4.3-mol/L trimethylamine aqueous solution was added to a solution of 3.5 g (3.9 mmol) of the halide intermediate (1) in 0 mL of acetonitrile. The resultant was heated and stirred at 100° C. for 17 hours in a pressure-resistant closed vessel. The reaction solution was allowed to cool to room temperature; thereafter, the solvent was concentrated under reduced pressure to thereby obtain 3.5 g of a quaternary salt intermediate (1). Then, 3.5 g of the obtained quaternary salt intermediate (1) was dissolved in 40 mL of ethanol; hydrazine monohydrate was slowly added, and thereafter stirred at 50° C. for 3 hours. After the termination of the reaction, the resultant was cooled to room temperature, diluted with 100 mL of ethanol, and filtered. A filtrate was concentrated under reduced pressure to thereby obtain 3.1 g of a tertiary amine intermediate (2). 3.0 g of the tertiary amine intermediate (2) was suspended in 20 mL of ion-exchange water; and a solution of 20 mL of ion-exchange water containing 2.3 g of lithium bistrifluoromethanesulfonylimide was slowly dropped. After 1 hour of stirring, the resultant was separated by decantation; and an obtained precipitate was washed with 10 mL of ion-exchange water to thereby obtain 3.8 g (4.3 mmol) (quant.) of a compound (2).

Figure 1:
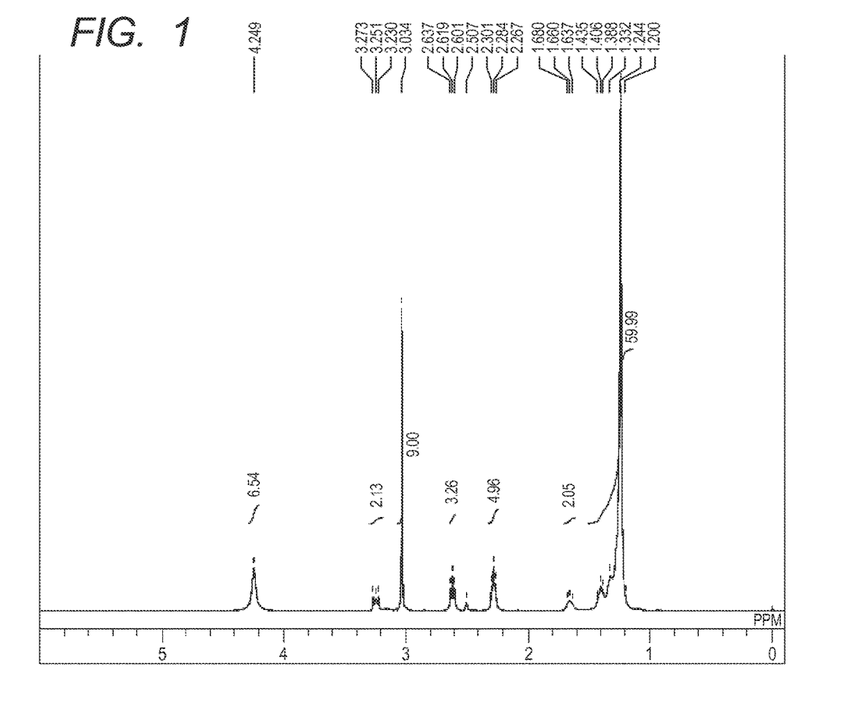
FIG. 1 is a diagram illustrating a $^1$H-NMR spectrum, in CDCl$_3$ at room temperature at 400 MHz, of a compound (2) which is one of the amine compounds having a structure represented by the general formula (1) according to the present invention.

In FIG. 1, a $^1$H-NMR spectrum in $CDCl_3$ at room temperature at 400 MHz of the compound (2) is illustrated.

[Analysis Results of the Compound (2)]

[1] $^1$H-NMR (400 MHz, DMSO-$d_6$, room temperature): δ (ppm)=1.20-1.44 (60H, m), 1.64-1.68 (2H, m), 2.27-2.30 (5H, m), 2.60-2.64 (3H, m), 3.03 (9H, s), 3.23-3.27 (2H, m), 4.25 (4H, br).

[2] Mass Spectrometry (ESI-TOF): m/z=890.6047 $(M+H)^+$.

Production Examples 2 to 4: Production of Compounds (3), (5) and (11)

Compounds (3), (5) and (11) were synthesized as in Production Example 1, except for using imides of the anionic compounds (5), (1) and (7), respectively, in place of lithium bistrifluoromethanesulfonylimide (the anionic compound (2)) in Production Example 1, and were identified by the above analyzers.

Production Example 5: Production of a Compound (4)

halide intermediate (2)

(3) quaternary salt-making step quaternary salt (2)

(4) Gabriel reactio step ↓ tertiary amine intermediate (3)

(5) anion exchange step 10 mL of a 4.3-mol/L trimethylamine aqueous solution was added to a solution of 6 g (8.8 mmol) of the halide intermediate (2) 30 mL of acetonitrile. The resultant was heated and stirred at 100° C. for 3.5 hours in a pressure-resistant closed vessel. The reaction solution was allowed to cool to room temperature; thereafter, the solvent was concentrated under reduced pressure to thereby obtain 7.0 g of a quaternary salt (2). Then, 7.0 g of the obtained quaternary salt (2) was dissolved in 90 mL of ethanol; 8.8 mL of hydrazine monohydrate was slowly added, and thereafter stirred at 50° C. for 3 hours. After the termination of the reaction, the resultant was cooled to room temperature, diluted with 100 mL of ethanol, and filtered. A filtrate was concentrated under reduced pressure to thereby obtain a tertiary amine intermediate (3). The obtained tertiary amine intermediate (3) was dissolved in 90 mL of ion-exchange water; and a solution of 70 mL of ion-exchange water containing 2.6 g of lithium bistrifluoromethanesulfonylimide was slowly dropped. The aqueous solution was extracted with 180 mL of dichloromethane, and concentrated under reduced pressure to thereby obtain 2.2 g (3.3 mmol) of a compound (4). The compound (4) was identified to be a target substance by the above analyzers.

Production Example 6: Production of a Compound (8)

5.5 g of a compound (8) was obtained by the same operation as in Production Example 5, except for using 6 mL of 1-methylimidazole in place of using the trimethylamine aqueous solution in Production Example 5. The compound (8) was identified to be a target substance by the above analyzers.

Example 1

<Production of a Urethane Resin Composition 1>
15.6 parts by mass of an isocyanate (trade name: Millionate MT, MDI, manufactured by Nippon Polyurethane Industry Co., Ltd.) and 2 parts by mass of the compound (2) were added to 84.4 parts by mass of a polyether polyol (trade name: EP505S, manufactured by Mitsui Chemicals, Inc.) so that the NCO equivalent weight was 1.4. Here, the NCO equivalent weight indicates a ratio ([NCO]/([OH]+[NH$_2$])) of the molar number of isocyanate groups in the isocyanate compound to the molar number of hydroxyl groups in the polyol component and the molar number of amino groups in the present amine compound. Then, methyl ethyl ketone (hereinafter, MEK) was added so that the total solid fraction ratio became 30% by mass, and mixed and stirred, and formed into a sheet form of 0.5 mm in thickness by a solvent casting method. Then, the sheet was heat treated in an oven heated to 120° C. for 3 hours to thereby produce a urethane resin composition 1 of a sheet form.

Examples 2 and 3

Urethane resin compositions 2 and 3 were produced by the same production method as in Example 1, except for using the compound (2) of parts by mass shown in Table 1 in place of using 2 parts by mass of the compound (2) in Example 1, and adjusting the amounts of the polyether polyol and the isocyanate to be added so that the NCO equivalent weight became 1.4.

Examples 4 to 6 and Examples 8 to 11

Urethane resin compositions 4 to 10 were produced by the same method as in Example 1, except for using compounds described in Table 1 in place of using the compound (2) in Example 1.

Example 7

2 parts by mass of the compound (2), 100 parts by mass of an epichlorohydrin-ethylene oxide-allyl glycidyl ether ternary copolymer (GECO) (trade name: Epichlomer CG-102, manufactured by Daiso Co., Ltd.), 5 parts by mass of zinc oxide, 35 parts by mass of calcium carbonate, 0.5 parts by mass of a carbon black (trade name: Seast S0, manufactured by Tokai Carbon Co., Ltd.) and 2 parts by mass of stearic acid were kneaded to thereby produce a rubber composition A.

0.5 parts by mass of sulfur and 1.5 parts by mass of dipentamethylenethiuramtetrasulfide (trade name: Nocceler TRA, manufactured by Ouchi Shinko Chemical Industrial Co., Ltd.) were added to the rubber composition A obtained in the above, and kneaded by an open roll to thereby produce a rubber composition B.

The rubber composition B was put in a metal mold for a 0.5 mm-thick sheet, and vulcanized by a heat press at 160° C. for 15 min. Then, a rubber sheet taken out from the metal mold was vulcanized in an oven at 160° C. for 1 hour to thereby produce a rubber composition 1.

Examples 12 and 13

Rubber compositions 2 and 3 were produced by the same method as in Example 7, except for using compounds described in Table 1 in place of using the compound (2) in Example 7.

Comparative Example 1

<Fabrication of a Comparative Resin Composition 1>
A comparative resin composition 1 was produced by the same production method as in Example 1, except for using no compound (2) in Example 1.

Comparative Examples 2 to 5

<Fabrication of Comparative Resin Compositions 2 to 5>
Comparative resin compositions 2 to 5 were produced by the same production method as in Example 1, except for using comparative compounds (1) to (4), respectively, in place of using the compound (2) in Example 1.

Comparative Examples 6 and 7

Comparative rubber compositions 1 and 2 were produced by the same method as in Example 7, except for using no compound (2) or using the comparative compound (1), respectively, in place of using the compound (2) in Example 7.

comparative compound (1)

comparative compound (2)

comparative compound (3)

comparative compound (4)

<Bleeding Test Evaluation>
The resin composition 1 was brought into contact with a polyethylene terephthalate (PET) sheet, and allowed to stand still under the environment of a temperature of 40° C. and a humidity of 95% RH for 1 week. The resin composition on the PET sheet surface was observed by an optical microscope (×10)(VHX-500, manufactured by Keyence Corp.). The evaluation was carried out as follows; and the case where the rate was B or higher was determined as no influence by bleeding. The evaluation results are shown in Table 1.

A: no bleeding substance is observed on the contacting portion.

B: slight cloudiness is observed on a part of the contacting portion.

C: slight cloudiness is observed on the whole surface of the contacting portion.

D: bleeding substances are observed and conspicuous on the whole surface of the contacting portion.

<Electroconductivity Change Evaluation>

Figure 2:
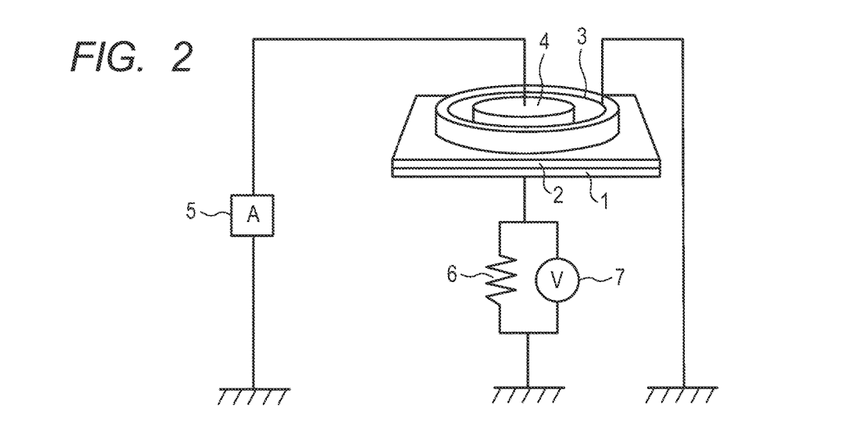
FIG. 2 is a view illustrating an outline of a current value measuring instrument for the resin composition according to the present invention.

An outline of a current value measuring instrument of a resin composition is illustrated in FIG. 2.

A resin composition 1 of 0.5 mm in thickness is brought into contact with a flat plate electrode 2 and with a cylindrical electrode 4 of 1 cm in diameter having a guard ring 3. Then, a direct current of 50 µA is impressed under the environment of a temperature of 23° C. and a humidity of 50% RH by a power source 5. The voltage impressed across a resistor 6 by the power source 5 after 2 sec of the current impression was measured for 3 sec by a voltmeter 7, and an initial volume resistance (Ω·cm) of the resin composition was calculated from the voltage averaged in time.

After a current of 50 µA was further impressed for 10 min, the voltage impressed across the resistor 6 by the power source 5 was measured for 3 sec by the voltmeter 7; and a volume resistivity (Ω·cm) after 10 min of the resin composition was calculated from the voltage averaged in time; and the volume resistivity after 10 min/the initial volume resistivity was taken as an electroconductivity change rate.

The case where the electroconductivity change rate was a value lower than 2.0 was determined to be excellent in electroconductivity.

A: the electroconductivity change rate was lower than 1.5 (the electroconductivity is excellent).

B: the electroconductivity change rate was 1.5 or higher and lower than 2.0 (the electroconductivity is good).

C: the electroconductivity change rate was 2.0 or higher (the electroconductivity is poor).

The results of Examples 1 to 13 and Comparative Examples 1 to 7 hitherto are shown in Table 1.

TABLE 1

| | Anionic Compound Used | Compound | parts by mass used of the Compound | Resin | Bleeding Evaluation | Initial Volume Resistivity (Ω · cm) | Electroconductivity Change Rate | Electroconductivity Change Evaluation |
|---|---|---|---|---|---|---|---|---|
| Example 1 | anionic compound (2) | Compound (2) | 2 | urethane resin composition 1 | A | 3.1E+07 | 1.23 | A |
| Example 2 | anionic compound (2) | Compound (2) | 10 | urethane resin composition 2 | A | 6.7E+06 | 1.51 | B |
| Example 3 | anionic compound (2) | Compound (2) | 25 | urethane resin composition 3 | B | 4.2E+06 | 1.83 | B |
| Example 4 | anionic compound (1) | Compound (3) | 2 | urethane resin composition 4 | A | 2.7E+07 | 1.31 | A |
| Example 5 | anionic compound (5) | Compound (5) | 2 | urethane resin composition 5 | A | 6.3E+07 | 1.21 | A |
| Example 6 | anionic compound (7) | Compound (11) | 2 | urethane resin composition 6 | A | 4.1E+07 | 1.15 | A |
| Example 7 | anionic compound (2) | Compound (2) | 2 | rubber composition 1 | B | 2.3E+07 | 1.66 | B |
| Example 8 | anionic compound (2) | Compound (4) | 2 | urethane resin composition 7 | A | 3.5E+07 | 1.26 | A |
| Example 9 | anionic compound (2) | Compound (4) | 10 | urethane resin composition 8 | A | 7.0E+07 | 1.55 | B |
| Example 10 | anionic compound (2) | Compound (8) | 2 | urethane resin composition 9 | A | 1.5E+07 | 1.18 | A |
| Example 11 | anionic compound (2) | Compound (8) | 10 | urethane resin composition 10 | A | 5.1E+06 | 1.37 | A |
| Example 12 | anionic compound (2) | Compound (4) | 2 | rubber composition 2 | B | 3.3E+07 | 1.71 | B |
| Example 13 | anionic compound (2) | Compound (8) | 2 | rubber composition 3 | B | 1.2E+07 | 1.47 | A |
| Comparative Example 1 | — | no addition | — | comparative resin composition 1 | — | 8.1E+08 | 5.36 | C |
| Comparative Example 2 | — | comparative compound (1) | 2 | comparative resin composition 2 | C | 2.3E+07 | 2.15 | C |
| Comparative Example 3 | — | comparative compound (2) | 2 | comparative resin composition 3 | D | 1.3E+08 | 3.88 | C |
| Comparative Example 4 | — | comparative compound (3) | 2 | comparative resin composition 4 | D | 2.1E+08 | 4.05 | C |
| Comparative Example 5 | — | comparative compound (4) | 2 | comparative resin composition 5 | C | 3.9E+07 | 2.41 | C |
| Comparative Example 6 | — | no addition | 2 | comparative rubber composition 1 | — | 5.1E+07 | 3.61 | C |
| Comparative Example 7 | — | comparative compound (1) | 2 | comparative rubber composition 2 | D | 3.2E+07 | 2.22 | C |

As is clear from Table 1, it has been found that the resin compositions using the amine compounds represented by the general formula (1) according to the present invention exhibited little bleeding and were excellent in electroconductivity as compared with the resin compositions fabricated by adding no amine compound or using the comparative compounds.

The present invention can provide an amine compound and an ionic conductive agent excellent in electroconductivity. Since an electroconductive resin composition suppressed in bleeding and excellent in electroconductivity is obtained from the amine compound, the resin composition can be utilized for liquid crystal displays, precision devices such as optical lenses, automobile parts, base materials for magnetic recording media such as optical discs, protection films for materials for semiconductors, coating materials, adhesives, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-101636, filed May 15, 2014, and Japanese Patent Application No. 2015-080042, filed Apr. 9, 2015, which are hereby incorporated by reference herein in their entirety.

What is claimed is:

1. An electroconductive resin composition comprising:
a resin selected from the group consisting of an ultraviolet curing resin, a rubber and a pressure-sensitive adhesive; and
an amine compound having an anion portion and a cation portion, the anion portion having a structure of:

wherein each of $R_9$ and $R_{10}$ is independently selected from the group consisting of a fluorine atom and a perfluoroalkyl group having 1 to 8 carbon atoms; and the cation portion having a structure of:

wherein:

each of $R_1$ to $R_3$ is, independently, an alkyl group having 1 to 20 carbon atoms;

each of $R_4$ to $R_7$ is independently selected from the group consisting of a hydrogen atom and an alkyl group having 1 to 20 carbon atoms;

$R_8$ is an unsubstituted aminoalkyl group having 1 to 20 carbon atoms; and each of n and m is, independently, an integer of 1 to 20.

2. The electroconductive resin composition according to claim 1, wherein each of $R_1$ to $R_3$ is an alkyl group having 1 to 4 carbon atoms.

3. The electroconductive resin composition according to claim 1, wherein each of $R_4$ to $R_7$ is a hydrogen atom.

4. The electroconductive resin composition according to claim 1, wherein each of $R_1$ to $R_3$ is a methyl group.

5. The electroconductive resin composition according to claim 1, wherein each of $R_9$ and $R_{10}$ is a perfluoroalkyl group having 1 to 8 carbon atoms.

6. The electroconductive resin composition according to claim 1, wherein each of $R_9$ and $R_{10}$ is a trifluoromethyl group.

7. The electroconductive resin composition according to claim 1, comprising a crosslinked product of the amine compound and a polyisocyanate compound.

\* \* \* \* \*